United States Patent [19]

Mattock

[11] 4,246,085
[45] Jan. 20, 1981

[54] FRACTIONATION OF PROTEINS

[75] Inventor: Patrick Mattock, Botley, England

[73] Assignee: United Kingdom Atomic Energy Authority, London, England

[21] Appl. No.: 112,109

[22] Filed: Jan. 14, 1980

[30] Foreign Application Priority Data

Feb. 16, 1979 [GB] United Kingdom ............... 05600/79

[51] Int. Cl.$^3$ ..................... G01N 27/26; A61K 35/14; A61K 35/16
[52] U.S. Cl. .......................... 204/180 R; 204/299 R; 23/230 B; 424/12
[58] Field of Search ........... 204/180 R, 180 S, 180 G, 204/180 P, 299, 301; 424/12; 23/230 B

[56] References Cited

U.S. PATENT DOCUMENTS

| 3,870,617 | 3/1975 | Bovrat | 204/301 |
| 3,989,613 | 11/1976 | Gritzner | 204/301 X |
| 4,149,957 | 4/1979 | Gibson et al. | 204/301 |

FOREIGN PATENT DOCUMENTS 1431888  4/1976  United Kingdom .

OTHER PUBLICATIONS

Chem. Abstracts, vol. 54, No. 1, 1-10-60, col. 672(b).
Chem. Abstracts, vol. 52, No. 21, 11-10-58, col. 18751 (g,h).

Primary Examiner—Arthur C. Prescott
Attorney, Agent, or Firm—Larson, Taylor and Hinds

[57] ABSTRACT

The invention is concerned with fractionation of proteins, in particular with fractionation of immunoglobulin containing solutions, such as blood plasma, by continuous flow electrophoresis.

Hitherto, such solutions have been fractionated by ethanol precipitation methods (e.g. the Cohn Method). Such methods separate the IgG component of immunoglobulins but cannot separate the useful IgM component. In the invention, the solutions are fractionated by continuous flow electrophoresis at a pH of between 7 and 8.4 and an electrical conductivity of between 1 and 2 mScm$^{-1}$, thereby giving rise to fractions containing particular combinations of immunoglobulin components (IgG, IgM, IgA, IgD and IgE) with potentially valuable properties.

4 Claims, No Drawings

FRACTIONATION OF PROTEINS

This invention relates to the fractionation of immunoglobulin containing solutions, such as blood plasma, by continuous flow electrophoresis.

The immunoglobulins constitute a family of complex proteins contained, for example, in blood plasma. They may be made up of several constituents each of which has different properties from the others in some respect or other. There are five main components found in immunoglobulins and these are usually designated as IgM, IgA, IgG, IgD and IgE respectively. Certain of the components may be separated by techniques known in the art such as an ethanol precipitation method known as the Cohn Method which separates the IgG component, but which cannot separate the IgM component which has antibacterial antibodies lacking in the IgG component.

We have now established conditions under which immunoglobulins may be fractionated by means of continuous flow electrophoresis and surprisingly found that certain of the fractions so obtained may be constituted by mixtures of certain components having particularly advantageous properties.

The present invention provides a method of fractionating an immunoglobulin containing aqueous solution which comprises the steps of (i) adjusting the pH of the aqueous solution to between 7 and 8.4 and the electrical conductivity thereof to between 1 and 2 $mScm^{-1}$ as measured at 20° C.;

(ii) subjecting the product of step (i) to continuous flow electrophoresis by injecting it as a migrant solution into a second aqueous solution, laminarly flowing in an annular separation chamber as a carrier solution for the migrant solution and stabilised by means of an angular velocity gradient, said carrier solution having a pH of between 7 and 8.4, and by applying a constant electric field across the resulting mixture to produce differential movement of the components of the immunoglobulin relative to themselves and to any other major components of the solution perpendicular to the direction of flow of the carrier solution; and (iii) collecting resulting particular fractions containing one or more components of the immunoglobulin.

The fractions may then, if desired, be concentrated e.g., by hollow fibre membrane concentrators, and then freeze dried. The fractions may be reconstituted in a small volume of liquid. Analysis of such reconstituted fractions for IgG, IgM, IgA, IgD and IgE components has shown that particular fractions may contain particular relative proportions of such components, which particular fractions may possess specific value for immunisation against specific infections. Further details are contained in the example of this specification.

Step (ii) is most conveniently carried out as generally described in U.K. Patent Specification No. 1,186,184 (corresponding to U.S. Pat. No. 3,616,453), which describes a process and apparatus where stabilisation of flowing streams in continuous flow electrophoresis is effected by an angular velocity gradient. Thus, in our invention, the fractionation may be effected in an annular separation chamber defined between a central stationary cylinder (a stator) and an outer rotating cylinder (a rotor), which results in a gradient of angular velocity across the annular chamber giving laminar flow at high throughputs. The constant electric field is then applied across the annular chamber to produce the differential movement of the immunoglobulin components of the migrant solution. Improvements and/or modifications of the apparatus described in U.K. Pat. No. 1,186,184 are described in U.K. patent specification Nos. 1,431,887 and 1,431,888 (corresponding to U.S. Pat. No. 3,844,926).

The pH of the migrant and carrier solutions in step (ii) is, as stated, between 7 and 8.4; very effective fractionation is found to occur in this range, which also enables factor VIII, and for albumin, if present, to be fractionated at the same time, e.g., where the aqueous solution comprises blood plasma. Separation of factor VIII by continuous flow electrophoresis is described in the specification of our International Patent Application No. PCT/GB78/00038, filed Nov. 10, 1978 (Agents' Reference 11925 M1H) which describes inter alia a method of purifying a factor VIII containing aqueous solution characterised by the steps of (i) reducing the ionic strength of the solution to a level such that it is capable of being electrophoresed;

(ii) adjusting the pH of the solution to within a range where the stability of Factor VIII is not adversely affected;

(iii) subjecting the product of step (ii) to continuous flow electrophoresis by injecting the solution as a migrant solution into a second aqueous solution, laminarly flowing in an annular separation chamber as a carrier solution for the migrant solution and stabilised by means of an angular velocity gradient, and applying a constant electric field across the resulting mixture to produce a differential movement of the factor VIII component of the migrant solution with respect to the other major components of the solution perpendicular to the direction of flow of the layer; and (iv) collecting the separated Factor VIII component.

It is surprising that our invention operates so satisfactorily when the migrant solution has a pH of 7.5. Thus, the isoelectric point of immunoglobulins are high (between about pH 7.5 and 8.5) and under conditions of electrophoresis at pH 7.5, it might be expected that the immunoglobulins would not exhibit any movement or that they might move into the membrane in the apparatus described in U.K Patent Nos. 1,431,887 and 1,431,888. This, however, does not happen in our experience.

A suitable buffer for the migrant solution is triscitrate and we prefer that its electrical conductivity is in the range of 0.75 to 1 $mScm^{-1}$ as measured at 20° C.

Step (iii) may be carried out as described in U.K. Patent Nos. 1,431,887 and 1,431,888. Thus, if our method is carried out as described in these specifications, the direction of migration of the migrant solution is centrifugal and the injection thereof accordingly effected at the inner side of the flow of the carrier solution. The direction of flow is generally upward and is helical in pattern because of the effect of the rotation of the rotor. Particular fractions may then be collected by means of an off-take system located in the stator and consisting of a series of parallel mazeplates with spacers. A particular fraction may then pass through one or more particular mazeplates and hence into collecting tube(s).

The invention will now be particularly described, by way of example only, as follows.

Example

Outdated frozen human blood plasma (250 ml) was thawed rapidly and dialysed overnight against an aqueous tris-citrate solution (10 L; pH 7.5; conductivity 1 mScm$^{-1}$) at 4° C. in order to reduce the salt concentration of the plasma. The dialysed plasma was then diluted approximately 1.5 times with an aqueous tris-citrate solution to give a product of pH 7.5 and an electrical conductivity of 1.0 mScm$^{-1}$ at 20° C.

The above product, as a migrant solution, was then warmed to 20° C. and electrophoresed using a continuous electrophoretic separation apparatus of the type generally described in U.K Patent Specification Nos. 1,431,887 and 1,431,888. The apparatus had 29 outlet ports, a stator radius of 40 mm, a rotor radius of 45 mm to give an annular gap of 5 mm, and electrodes 304 mm in length. A carrier solution at 2° C. comprising an aqueous tris-citrate solution (pH 7.5; electrical conductivity 0.75 mScm$^{-1}$ at 20° C.) was passed upwardly through the annular gap at a rate of 500 ml/minute and the flow stabilized by rotation of the rotor. The migrant solution was injected into the annular gap at a rate of 10 ml/minute. The electrophoresis was carried out at 35 amps and 27 volts giving a temperature rise of carrier solution of 20° C., i.e., from 2° C. to 22° C. The electrolytes were ammonium acetate (1 M; pH 7.5) for the cathode and an equal volume mixture (pH 7.5) of ammonium citrate (0.2 M) and ammonium phosphate (0.15 M) for the anode.

The particular fractions were each collected and concentrated by hollow fibre membrane concentrators and then freeze dried. Each fraction was re-constituted in a small volume of distilled water and analysed for the immunoglobulin components IgG, IgM, IgA, IgD and IgE by quantitative immunoelectrophoresis. The results are shown in Table I below as percentage of activity per minute per off-take.

TABLE 1

| Fraction No | IgG | IgM | IgA | IgD | IgE |
|---|---|---|---|---|---|
| 1 | 0.9 | 0.1 | | | |
| 2 | 3.1 | 0.3 | | | |
| 3 | 7.4 | 0.6 | | | 0.2 |
| 4 | 8.6 | 1.9 | | | 0.4 |
| 5 | 6.5 | 4.0 | | 0.4 | 0.6 |
| 6 | 6.8 | 5.7 | 0.1 | 1.2 | 0.5 |
| 7 | 6.8 | 5.9 | 0.2 | 1.7 | 0.8 |
| 8 | 10.1 | 9.0 | 0.7 | 5.2 | 1.4 |
| 9 | 14.1 | 17.5 | 3.4 | 15.6 | 5.2 |
| 10 | 10.0 | 16.1 | 6.6 | 20.3 | 7.8 |
| 11 | 9.6 | 16.4 | 15.0 | 23.4 | 20.2 |
| 12 | 6.7 | 9.0 | 17.9 | 12.7 | 24.0 |
| 13 | 4.5 | 6.4 | 20.0 | 10.8 | 15.6 |
| 14 | 3.2 | 4.5 | 21.1 | 5.8 | 15.0 |
| 15 | 1.9 | 2.7 | 15.0 | 2.8 | 8.5 |

It will be seen that, apart from IgG which shows a broad spread across about 15 fraction numbers, the bulk of the remaining immunoglobulin components are present in about six fraction numbers, specifically 8 to 13. Also, it will be noted that at the pH of this example (7.5) the mobilities of the immmunoglobulin components are sufficiently different for fractions to be collected in order to maximise the proportion of any one particular component, The order of decreasing mobility is IgA, IgE, IgD, IgM and IgG. Table II below shows how fractions may be combined in order to obtain mixtures of immunoglobulin components of various composition.

TABLE II

| Fractions Numbers Combined | Immunoglobulin | Total % |
|---|---|---|
| 1-7 | IgG | 40 |
| | IgM | 20 |
| | IgG | 45 |
| | IgM | 60 |
| 8-11 | IgA | 25 |
| | IgD | 65 |
| | IgE | 35 |
| | IgG | 15 |
| | IgM | 20 |
| 12-15 | IgA | 75 |
| | IgD | 35 |
| | IgE | 65 |

Certain of the fractions obtained were combined and analysed for specific antibodies, namely anti-tetanus, anti-measles, anti-rubella and anti-polio virus type III. The techniques used for analysis were radial immunodiffusion for anti-tetanus antibodies, haemaglutination inhibition tests for anti-measles and anti-rubella antibodies, and tissue culture neutralization tests for anti-polio virus type III antibodies. The results are shown in Table III below.

TABLE III

| Fractions Numbers (combined) | Specific Antibodies (%/fraction) | | | |
|---|---|---|---|---|
| | Tetanus | Measles | Rubella | Polio virus Type III |
| 1, 2 | 17.7 | 16.6 | 17.5 | 22.6 |
| 3, 4 | 31.5 | 44.2 | 51.1 | 30.2 |
| 5, 6 | 23.5 | 17.4 | 20.2 | 16.9 |
| 7, 8 | 13.8 | 12.5 | 7.2 | 12.3 |
| 9, 10 | 9.4 | 5.0 | 2.9 | 9.7 |
| 11, 12 | 4.1 | 4.4 | 1.2 | 8.4 |

It will be seen that the anti-bodies are principally contained in the early fractions up to fraction 6. These early fractions contain mainly the IgG and IgM components (see Table I). Thus, by combining specific fractions in a pool, high specific activity anti-body preparations can be prepared simply, leaving the other fractions for other uses. Also, IgM, which is a large molecular weight immunoglobulin, tends to possess good antibacterial properties and fractions containing it might be used in treatment where the prime aim is to obtain immunity against certain bacterial infections.

It should be noted that the fractions obtained were not necessarily pure. Thus, from fraction numbers 8 to 10 and higher, other plasma proteins were present including fibrinogen which may be removed by other means. This though is probably not of great practical importance. However, albumin, the major plasma protein, was well separated and all of the fractions were albumin free.

I claim:

1. A method of fractionating an immunoglobulin-containing aqueous solution which comprises the steps of
   (i) adjusting the pH of the aqueous solution to between 7 and 8.4 and the electrical conductivity thereof to between 1 and 2 mScm$^{-1}$ as measured at 20° C.;
   (ii) subjecting the product of step (i) to continuous flow electrophoresis by injecting it as a migrant solution into a second aqueous solution, laminarly flowing in an annular separation chamber as a carrier solution for the migrant solution and stabilized by means of an angular velocity gradient, said carrier solution having a pH of between 7 and 8.4, and by applying a constant electric field across the resulting mixture to produce differential movement of the components of the immunoglobulin relative to themselves and to any other major components of the solution perpendicular to the direction of flow of the carrier solution; and (iii) collecting resulting particular fractions containing one or more components of the immunoglobulin.

2. A method according to claim 1 wherein, in step (1), the pH of the aqueous solution is adjusted to 7.5 and the electrical conductivity thereof to 1 $mScm^{-1}$ as measured at 20° C.

3. A method according to claim 1 wherein the migrant solution has an electrical conductivity in the range of 0.75 to 1 $mScm^{-1}$ as measured at 20° C.

4. A method according to claim 1 wherein the immunoglobulin-containing aqueous solution comprises blood plasma.

* * * * *